United States Patent
Beaussoubre et al.

(10) Patent No.: US 10,662,395 B2
(45) Date of Patent: May 26, 2020

(54) ODOR NEUTRALIZER FOR AMMONIA AND PRIMARY OR SECONDARY AMINES

(71) Applicant: Firmenich SA, Geneva (CH)

(72) Inventors: Pascal Beaussoubre, Geneva (CH); Wolfgang Fieber, Geneva (CH)

(73) Assignee: Firmenich SA, Meyrin (CH)

( * ) Notice: Subject to any disclaimer, the term of this patent is extended or adjusted under 35 U.S.C. 154(b) by 223 days.

(21) Appl. No.: 15/768,054

(22) PCT Filed: Nov. 16, 2016

(86) PCT No.: PCT/EP2016/077913
§ 371 (c)(1),
(2) Date: Apr. 13, 2018

(87) PCT Pub. No.: WO2017/085152
PCT Pub. Date: May 26, 2017

(65) Prior Publication Data
US 2018/0320107 A1    Nov. 8, 2018

(30) Foreign Application Priority Data
Nov. 16, 2015   (EP) ..................................... 15194665

(51) Int. Cl.
*C11B 9/00* (2006.01)
*A61K 8/49* (2006.01)
*A61L 9/14* (2006.01)
*A61Q 15/00* (2006.01)
*C11D 3/20* (2006.01)
*A61L 9/04* (2006.01)
*A61L 9/12* (2006.01)
*A61L 9/012* (2006.01)
*A61L 2/16* (2006.01)
*A61Q 5/00* (2006.01)

(52) U.S. Cl.
CPC .......... *C11B 9/0076* (2013.01); *A61K 8/4973* (2013.01); *A61L 2/16* (2013.01); *A61L 9/012* (2013.01); *A61L 9/048* (2013.01); *A61L 9/122* (2013.01); *A61L 9/127* (2013.01); *A61L 9/14* (2013.01); *A61Q 5/00* (2013.01); *A61Q 15/00* (2013.01); *C11D 3/2096* (2013.01); *A61L 2209/132* (2013.01)

(58) Field of Classification Search
None
See application file for complete search history.

(56) References Cited

U.S. PATENT DOCUMENTS

2004/0259751 A1   12/2004   Kessler et al.
2006/0009368 A1    1/2006   Noerenberg et al.

FOREIGN PATENT DOCUMENTS

| DE | 19858812 A1 | 6/2000 |
|---|---|---|
| EP | 1060737 A1 | 12/2000 |
| EP | 1122302 A1 | 8/2001 |
| EP | 2380958 A1 | 10/2011 |
| JP | H02302258 A | 12/1990 |
| JP | 2001294890 A | 10/2001 |
| WO | 01/55497 A1 | 8/2001 |
| WO | 03/048293 A1 | 6/2003 |
| WO | 2004031167 A1 | 4/2004 |

OTHER PUBLICATIONS

International Search Report from PCT Application No. PCT/EP2016/077913, dated Feb. 1, 2017.

*Primary Examiner* — Robert A Wax
*Assistant Examiner* — Randeep Singh
(74) *Attorney, Agent, or Firm* — Paul Zagar

(57) ABSTRACT

The present invention relates to the field of perfumery and more particularly to the field of malodor counteractancy. In particular, it relates to the use of glycerol carbonate or glycerol carbonate derivatives to neutralize the odor from ammonia and primary or secondary amines. Perfuming compositions and perfuming consumer products comprising those malodour neutralizers are also objects of the invention.

13 Claims, 3 Drawing Sheets

● Glycerol carbonate methyacrylate;

■ Glycerol carbonate;

○ Ethylene carbonate;

◊ Propylene carbonate;

△ Butylene carbonate

■ Glycerol carbonate;

◊ PEG methylester methacrylate

ODOR NEUTRALIZER FOR AMMONIA AND PRIMARY OR SECONDARY AMINES

RELATED APPLICATIONS

This application is a national stage application under 35 U.S.C. § 371 filing of International Patent Application PCT/EP2016/077913, filed 16 Nov. 2016, which claims the benefit of European patent application no 15194665.4 filed 16 Nov. 2015.

TECHNICAL FIELD

The present invention relates to the field of perfumery and more particularly to the fields of malodor counteractancy. In particular, it relates to the use of glycerol carbonate or glycerol carbonate derivatives to neutralize malodor, in particular from ammonia and primary or secondary amines. Perfuming compositions and perfuming consumer products comprising those compounds are also objects of the invention.

PRIOR ART

Offensive odors known as malodors are largely present in the surrounding environment and are constituted of complex mixtures of volatile organic compounds. The composition of malodors depends on the source generating them such as sweat, garbage, bathroom, kitchen, pet waste, waste water plant or body odor. These volatile organic compounds belong to different chemical families, including amines, carboxylic acids, alcohols, aldehydes and ketones or thiols, sulfides and disulfides.

The multiplicity of chemical constituents of malodor complex mixtures and the variety of sources of malodors has led to the development of different methods to reduce or suppress the malodor perception. These methods can be divided in three groups corresponding to different approaches. The first one addresses prevention of malodor formation, e.g. by using antimicrobial compounds which aim at suppressing or reducing the activity of microorganisms at the origin of malodor generation. The second approach relates to the sensory modification of the malodors, by using perfumery ingredients to cover them. The third approach tackles the elimination or neutralization of the malodors, e.g. by using an ingredient which will chemically and/or physico-chemically interact with the malodor compounds.

This latter method has been, among other, used to overcome malodors generated by ammonia and amine-containing compounds which are found in a large amount of malodor complex mixtures, typically in kitchen, garbage or bathroom. In this context U.S. Pat. No. 6,015,550 discloses the use of alkylene carbonate to reduce the odor of amine-containing compounds. Also, propylene carbonate has been disclosed in WO9946350 and JP02302258 wherein the reduction of the odor from amine-containing compound is due to the reaction between propylene carbonate and odorous amine.

In spite of the prior art methods to neutralize malodor, there is still a need to provide compounds more reactive toward amines to reduce the perceived malodor from ammonia and primary or secondary amines. In particular, there is still a need to increase speed of said reaction. The present invention provides a solution to the above mentioned problem by using glycerol carbonate or glycerol carbonate derivatives to reduce malodour from this class of compounds. Use of those compounds in this context have not been disclosed or suggested heretofore.

SUMMARY OF THE INVENTION

The invention relates to the use of glycerol carbonate or glycerol carbonate derivatives to neutralize malodors in particular generated by ammonia and primary amines or secondary amines. Unexpectedly, it has been found that said compounds are particularly efficient in reacting with those malodorous compounds and so to eliminate the related malodor irreversibly.

A first object of the present invention is therefore the use as malodor neutralizer in particular of malodors from ammonia and primary amines or secondary amines of a compound of formula (I)

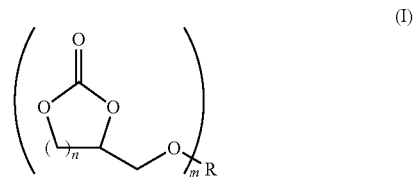

(I)

wherein m is an integer comprised from 1 to 4; n is 1 or 2; and R represents a hydrogen atom or a $C_{1-20}$ hydrocarbon group, preferably a $C_{1-10}$ hydrocarbon group, said hydrocarbon optionally comprising one or two oxygen or nitrogen atoms.

A second object of the present invention is a malodor neutralizing composition comprising
a) at least one compound of formula (I) as defined above;
b) at least one ingredient selected from the group consisting of a carrier, a perfumery ingredient, a perfumery adjuvant and a mixture thereof; and
c) optionally a malodor counteracting composition.

Another object of the present invention is a malodor neutralizing consumer product comprising a composition as defined above.

A last object of the present invention is a method to neutralize malodor in particular from ammonia and primary amines or secondary amines, which comprises dispensing into a closed space, or applying to a surface an effective amount of at least compound of formula (I) as defined above.

DESCRIPTION OF THE INVENTION

Figure 1:
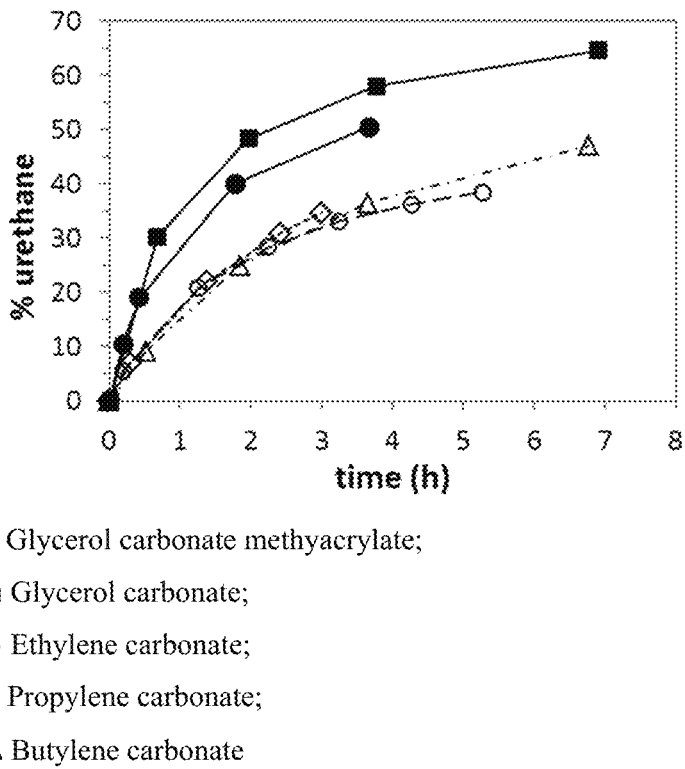
FIG. 1: Represents the conversion of iso-amylamine in presence of different cyclocarbonate molecules over time.

We have now surprisingly established that glycerol carbonate or glycerol carbonate derivatives possess very useful malodor counteracting properties by way of neutralizing particular malodour generating compounds. In the context of the invention "neutralizer" or "neutralizing" is referring to a particular mechanism including chemical and/or physico-chemical interaction with the identified malodor compounds. The use of the neutralizing compounds according to the present invention allows decreasing or suppressing the amount of malodor in particular ammonia and primary or secondary amines responsible of malodors very efficiently.

Advantageously the carbonate functional group of the neutralizing compounds is particularly reactive to bind irreversibly with the ammonia and primary or secondary amines responsible of malodor leading to a drop of the concentration of these chemicals in the surrounding environment. Unexpectedly, the perception of malodors using compounds of the present invention diminishes more rapidly that known compounds having the same mode of action. This effect is perceived as soon as the odor neutralizer of the present invention is used.

Therefore, a first object of the present invention is the use as malodor neutralizer in particular for ammonia and primary amines or secondary amines of a compound of formula

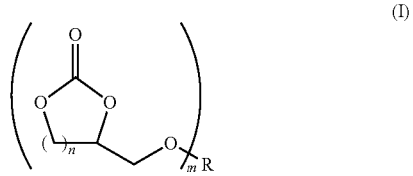

(I)

wherein m is an integer comprised from 1 to 4; n is 1 or 2; and R represents a hydrogen atom or a $C_{1-20}$ hydrocarbon group, preferably a $C_{1-10}$ hydrocarbon group, said hydrocarbon optionally comprising one or two oxygen or nitrogen atoms. According to any embodiment of the invention, compounds of formula (I) are in a form of any one of its stereoisomers or of any mixture thereof.

By the term primary amines or secondary amines, it is meant the normal meaning in the art, i.e. primary amine functional groups wherein a nitrogen atom is substituted by two hydrogen atoms and one hydrocarbyl group and secondary amine functional groups wherein a nitrogen atom is substituted by one hydrogen atoms and two hydrocarbyl group. Non-exhaustive examples of the primary or secondary amines which are known to be present in malodor complex mixtures are 3-methylbutylamine, butan-1-amine, 1,5-diaminopentane or 1,4-diaminobutane.

For the sake of clarity, by the expression "any one of its stereoisomers", or the similar, it is meant the normal meaning understood by a person skilled in the art, i.e. that the invention's compound can be a pure enantiomer (if chiral) or diastereoisomer.

For the sake of clarity, by the expression " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies. It is well understood by the person skilled in the art that when m is 1, R is a $C_{1-20}$ hydrocarbonyl group; when m is 2, R is a $C_{1-20}$ hydrocarbonediyl group; when m is 3, R is a $C_{1-20}$ hydrocarbonetriyl group and when m is 4, R is a $C_{1-20}$ hydrocarbonetetrayl group.

For the sake of clarity, by the expression "containing one or two oxygen atoms and/or one to two nitrogen atoms", or the similar, in the present invention it is meant that the group, to which is made reference, may include functional groups such as for examples, ethers, acetals, esters, aldehydes, ketones, amides, carboxylates or alcohols; preferably functional groups such as ethers, acetals, esters, amides, carboxylates or alcohols.

According to any one of the above embodiments of the invention, said compounds (I) are $C_4$-$C_{18}$ compounds.

According to any one of the above embodiments of the invention, m is 1 or 2. Preferably, m is 1.

According to any one of the above embodiments of the invention, n is 1.

According to any one of the above embodiments of the invention, R represents a hydrogen atom or a $C_{1-20}$ hydrocarbon group, in particular a $C_{1-10}$ hydrocarbon group or even a $C_{3-8}$ hydrocarbon group, said hydrocarbon optionally comprising one or two oxygen.

According to any one of the above embodiments of the invention, R represents a hydrogen atom, a methacryloyl group, a meta- or para-terephthaloyl group or a meta- or para-bezenediyl group.

According to any one of the above embodiments of the invention, when m is 1, R represents a hydrogen atom or a methacryloyl group, preferably a hydrogen atom.

According to any one of the above embodiments of the invention, when m is 2, R represents para-terephthaloyl group or a meta-benzenediyl group.

According to any one of the above embodiments of the invention, the compound of formula (I) is selected from the group consisting of 4-(hydroxymethyl)-1,3-dioxolan-2-one (called also glycerol carbonate), (2-oxo-1,3-dioxolan-4-yl) methyl methacrylate, 4,4'-((1,3-phenylenebis(oxy))bis (methylene))bis(1,3-dioxolan-2-one) and bis((2-oxo-1,3-dioxolan-4-yl)methyl) terephthalate. Preferably, the compound of formula (I) is 4-(hydroxymethyl)-1,3-dioxolan-2-one. Preferably, the compound of formula (I) is selected from the group consisting of (2-oxo-1,3-dioxolan-4-yl)methyl methacrylate, 4,4'-((1,3-phenylenebis(oxy))bis (methylene))bis(1,3-dioxolan-2-one) and bis((2-oxo-1,3-dioxolan-4-yl)methyl) terephthalate.

The compounds of formula (I) are commercially available or can be obtained by esterification or etherification of 4-(hydroxymethyl)-1,3-dioxolan-2-one using methods known by the person skilled in the art.

According to any one of the above embodiments of the invention, the compounds of formula (I) may be used in combination with compounds or technologies known to reduce or suppress the malodor perception having same or different mode of action than compounds of the present invention. As non-limiting example, the compounds of formula (I) may be used in combination with an absorbent material such as a material obtained from the processed corncob as described in EP1145723 or with the malodor counteracting composition as disclosed in WO2008155683. According to another particular embodiment, the compounds of formula (I) may be used in combination with a malodor counteracting (MOC) composition comprising at least one ingredient selected from Group (I) compounds, at least one ingredient selected from Group (II) compounds, and at least one ingredient selected from Group (III) compounds, wherein the Groups (I) to (III) compounds are defined as follows:

a) Group (I): aldehydes of formula $R^1CHO$, wherein $R^1$ is an aliphatic linear or branched, saturated or unsaturated carbon chain containing from 1 to 12 carbon atoms;
b) Group (II): ketones of formula $R^2COR^3$, wherein $R^2$ is an ethyl or methyl group and $R^3$ is an aliphatic linear or branched, saturated or unsaturated carbon chain containing from 1 to 12 carbon atoms;
c) Group (III): primary alcohols of formula $R^4CH_2OH$, wherein $R^4$ is an aliphatic linear or branched, saturated or unsaturated carbon chain containing 1 to 12 carbon atoms, optionally substituted with an aromatic moiety.

As shown in the examples below, the compounds of formula (I) are able to neutralize malodors in particular from ammonia and primary or secondary amines more rapidly than compounds known from the prior art and so have a better impact on the corresponding malodor. Without being bound by theory, it is believed that the compounds of formula (I) react with the odorous amines compound forming an urethane compound. The amines are irreversibly covalently bonded and so the concentration of the malodorous amines in the surrounding shall decrease.

In another aspect, the invention concerns the use of compounds of formula (I) described above in a malodor neutralizing composition or a malodor neutralizing consumer product for neutralizing malodor generated in particular by ammonia and primary or secondary amines. Therefore a method to reduce or neutralize malodour in particular from ammonia and primary or secondary amines, by irreversibly covalently binding the ammonia or the amine functional group, comprising dispensing an effective amount of compounds of formula (I) as defined above into a closed space or applying them onto a surface is also an object of the invention. Preferably, the invention's method comprises dispensing into a closed space the effective amount of compounds of formula (I) as defined above.

The compounds of formula (I) of the invention being advantageously used for reducing or suppressing the offensive odor of ammonia, primary or secondary amines, it is therefore particularly advantageous to include these compounds in a malodor neutralizing composition or in a consumer product. Ways to dispense into the air or apply onto a surface a composition or consumer products comprising compounds of formula (I) can be numerous. According to a preferred embodiment, the compositions or consumer products are dispensed in a closed space by means of a device dispensing the malodor neutralizing composition comprising compound of formula (I) into the air either as droplets which transition to vapor, or directly evaporating from a source. Devices that may introduce compositions comprising at least one compound of formula (I) to the air as droplets include: aerosol sprays, or atomizers; wall plug-ins or battery-powered devices that employ piezoelectric technology to aerosolize the composition; and, nebulization systems which convert liquid composition into a vapor normally without the use of heat. Devices that can introduce a composition comprising compounds of formula (I) to the air include also impregnated gels which release fragrance as the gel evaporates sometimes with the help of an electric fan; wick and reed diffusers which release compound of formula (I) by evaporation from compound of formula (I)—soaked wicks or wooden reeds; and, compound of formula (I) impregnated solid or semi-solid materials like paper, plastics, plaster and wood.

The aerosol spray uses a propellant and a composition comprising at least one compound of formula (I) packaged under pressure in a sealed metal or glass container with a valve which is opened by pressing down a button which contains a spray nozzle—the actuator. When the container's valve is opened by pressing the actuator, compound of formula (I) is forced through the spray nozzle located inside the actuator to create a mist of droplets containing compound of formula (I). The propellant may be a liquefied gas such as propane, butane or dimethyl ether; or, it may be a compressed gas such as compressed air or compressed nitrogen.

A relatively recent type of aerosol package also suitable in the context of the invention comprises a plastic bag filled with a composition comprising at least one compound of formula (I) contained within a can. The bag is attached to the valve/actuator/spray nozzle and sealed in the can surrounded by air under pressure. When the actuator is pressed, the valve opens and the liquid composition is forced through the nozzle by the pressure around the bag.

Also suitable for the present invention are automatic aerosol dispenser devices for intermittently releasing a dose of an aerosol from an aerosol can to the surroundings. These devices generally comprise a housing, which comprises: an aerosol container containing the composition comprising at least one compound of formula (I) under pressure; a release mechanism adapted to release the dose of aerosol from the can to the environment when actuated; an outlet connected to the aerosol release mechanism permitting the releasing of the dose of aerosol through the housing; an actuating mechanism adapted to actuate the aerosol release mechanism intermittently; and, a timing mechanism for controlling the interval of time between actuations.

The atomizer system comprises a plastic, glass or metal container of malodor neutralizing composition comprising at least one compound of formula (I) and a pump actuator. This operates in a similar fashion to an aerosol but the liquid composition is not packed under pressure. The pressure to atomize/aspirate the composition is created by the user of the product pressing the pump or pulling a trigger. This action creates sufficient pressure to draw the liquid stored in the container through a tube and into the actuator and spray nozzle. The mist created comprises droplets that are generally larger than those created using an aerosol spray device.

Piezoelectric technology is one of a number of electromechanical processes that exist for the generation of droplets. One method for such distribution is to atomize a liquid by a device comprising a perforated structure which is vibrated by an electromechanical transducer which has a composite thin-walled or planar structure, and is arranged to operate in a bending mode. Liquid is supplied to the vibrating perforated structure and sprayed therefrom in droplets upon vibration of the perforated structure.

Nebulizing scent delivery devices comprise an atomizer to atomize a liquid into a scented mist and deliver the scented mist to air outside of the atomizer.

Also suitable to the invention are a large variety of plug-in electrical devices that evaporate a malodor neutralizing composition into the surrounding air. Generally, these devices consist of a volatile composition; an electrical heater; and, a power supply. By the application of heat to the source, there is a continuous supply of the volatile composition to the space in which the device is placed According to particular embodiment, the device according to the invention is selected from the group consisting of an aerosol and an automatic aerosol spray.

According to an embodiment, the device of the invention consists of a spraying device.

Therefore, another object of the present invention is a malodor neutralizing composition comprising:
  i) at least one compound of formula (I) as defined above;
  ii) at least one ingredient selected from the group consisting of a carrier, a perfumery adjuvant and a perfumery ingredient; and
  iii) optionally at least one malodour counteracting composition.

According to a preferred embodiment, the malodor neutralizing composition consists of:
  i) at least one compound of formula (I) as defined above;
  ii) at least one ingredient selected from the group consisting of a carrier, a perfumery adjuvant and a perfumery ingredient; and
  iii) optionally at least one malodour counteracting composition.

By "carrier" we mean here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system (non-ionic, anionic, cationic, amphoteric or mixtures of), or a solvent commonly used in perfumery. A detailed description of the nature and type of solvents commonly used in perfumery cannot be exhaustive. However, one can cite as non-limiting examples solvents and in addition of solvent usable to form a capsule previously cited, such as dipropyleneglycol, 2-(2-ethoxyethoxy)-1-ethanol. For the compositions which comprise both a perfumery carrier and a perfumery co-ingredient, other suitable perfumery carriers than those previously specified, can be also ethanol, water, water/ethanol mixtures, propylene glycol, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique. Another solid carried may be an absorbent material obtained from the processed corncob as described in EP1145723. Said carried is a mixture of cellulose, hemicellulose and lignin and is formed by particles obtainable from a ring or fraction of a corncob having a content of less than 1% of fines by weight and a moisture content below 10% wherein the ring or fraction is selected from the group consisting of the woody ring with a particle size ranging between 250 and 2380 microns, the chaff ring with a particle size ranging between 73 and 841 microns, and a combination thereof.

A "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor, e.g. masking or neutralizing unpleasant odors. For the sake of clarity, the definition of perfuming ingredient is meant to include also pro-perfumes, i.e compounds which upon decomposition liberate a perfuming ingredient. A "perfuming composition" is a mixture of compounds including at least two perfuming co-ingredients.

In general terms, these perfuming ingredients belong to chemical classes as varied as alcohols, lactones, aldehydes, ketones, esters, ethers, ester nitriles, terpenoids, nitrogenous or *sulphurous* heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product.

According to any one of the above embodiment, the perfuming ingredients do not comprise a primary or secondary amino functional group.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers agents), colour agents (e.g. dyes and/or pigments), pH regulator.

An invention's composition consisting of the compound of formula (I) as defined above and at least one carrier represents a particular embodiment of the invention. By malodour counteracting composition, it is meant a composition that does not comprise a compound of formula (I) but which provides some malodour counteractancy and can be used to complement the neutralizing effect provided by compounds of formula (I). Examples of such compositions are provided here-above.

According to a particular embodiment, the invention's composition comprises at least one compound of formula (I) as defined above in an amount comprised between 0.1% and 50% by weight, relative to the total weight of the composition and at least one solid carrier as defined above. Preferably, the solid carrier is an absorbent material obtained from the processed corncob. Furthermore, compound of formula (I) as defined above or a malodor composition comprising at least one compound of formula (I) can also be advantageously used in consumer products in particular perfumed consumer products to prevent the malodor formation and/or to positively impart or modify the odor of a consumer product and into which said compound of formula (I) as defined above are added.

As shown in the examples below, the compound of formula (I) of the invention allow to neutralize or eliminate the odor from ammonia, primary and secondary amines.

Consequently, another object of the present invention is represented by a malodor neutralizing consumer product comprising, as malodor counteracting compound, compound of formula (I) as defined above.

For the sake of clarity, it has to be mentioned that, by "malodor neutralizing consumer product" it is meant a consumer product which is expected to deliver at least malodor counteractancy when applied to the surface to which it is applied (e.g. hair, textile, or home surface) or in the ambient air. In other words, such consumer product according to the invention is a product which comprises the functional formulation, a perfume, as well as optionally additional benefit agents, corresponding to the desired consumer product, e.g. a detergent or an air freshener, and an olfactive effective amount of at least one compound of formula (I). For the sake of clarity, said consumer product is a non-edible product.

The nature and type of the constituents of the consumer product do not warrant a more detailed description here, which in any case would not be exhaustive, the skilled person being able to select them on the basis of his general knowledge and according to the nature and the desired effect of said product.

Non-limiting examples of suitable consumer product can be a fabric care product, such as a liquid or solid detergent, a fabric softener, a fabric refresher, an ironing water, a paper, a bleach, carpet cleaners or curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a vanishing cream, a deodorant or antiperspirant, hair remover, tanning or sun product, nail products, skin cleansing or a makeup); or a skin-care product (e.g. a perfumed soap, shower or bath mousse, oil or gel, a hygiene product or foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or hard-surface detergent; a leather care product or a car care product, such as a polish, waxes or a plastic cleaners; a pet product in the form of absorbent pads, liners, cleansers and refreshing and perfuming sprays and products.

More preferably the consumer product can be a fabric care product, such as a liquid or solid detergent, a fabric softener, a fabric refresher, an ironing water, a hair care product such as a shampoo, a coloring preparation or a hair spray; an air care product, such as an air freshener or a "ready to use" powdered air freshener; or a home care product, such as a dish detergent or hard-surface detergent or refresher; or a malodor neutralizing sanitary product; or a pet product in the form of absorbent pads, liners, cleansers and refreshing and perfuming sprays and products. More preferably, the consumer product is a fabric softener, a fabric refresher, an ironing water, an air freshener, a "ready to use" powdered air freshener, a shampoo, a coloring preparation, a hair spray, or a cat litter. Even more preferably, the consumer product is an ironing water, an air freshener, a "ready to use" powdered air freshener, a coloring preparation, or a cat litter. Even more preferably, the perfuming consumer product is an air freshener, a "ready to use" powdered air freshener, a coloring preparation or a cat litter. Even more preferably, the perfuming consumer product is an air freshener, a "ready to use" powdered air freshener or a cat litter.

The proportions in which the compounds of formula (I) according to the invention can be incorporated into the various aforementioned articles or compositions vary within a wide range of values. These values are dependent on the nature of the article and on the desired organoleptic effect as well as the nature of the co-ingredients in a given base when the microcapsules according to the invention are mixed with perfuming co-ingredients, solvents or additives commonly used in the art.

For example, in the case of malodor neutralizing compositions, typical concentrations are in the order of 0.1% to 99% by weight, preferably from 0.1% to 80% by weight, more preferably from 0.1% to 50% by weight, even more preferably from 0.1% to 20% by weight of the compound of formula (I) based on the weight of the composition into which they are incorporated. Concentrations lower than these, such as in the order of 0.01% to 1% by weight, can be used when these compound of formula (I) are incorporated into perfumed articles, percentage being relative to the weight of the article.

Formulations of consumer product bases in which the compound of formula (I) can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in handbooks such as for example; CTFA Cosmetic ingredient handbook, $10^{th}$ edition or more recent versions; Formulating detergents and personal care products: a guide to product development (2000); as well as in the abundant patent literature in the field of body care and home care consumer products.

EXAMPLES

The following non limiting examples are further illustrative of the present invention embodiments, and further demonstrate the advantages of the invention relative to prior art teachings.

Abbreviations have the usual meaning in the art and the temperatures are indicated in degrees centigrade (° C.).

Example 1

NMR Monitoring of the Reaction of Compounds of Formula (I) Compared to Prior Art Cyclocarbonate Compounds with iso-amylamine in Solution 0.5 mol/l of iso-amylamine is dissolved in NMR solvent methanol-d4. An equimolar amount of cyclocarbonate is added, and the mixture is transferred to an NMR tube. A series of quantitative $^1$H NMR spectra is carried out at 25°

C. Alkylene carbonates according to prior art (ethylene, propylene, butylene carbonate) display a similar kinetic of reaction: after 1 hour, the trend of the measurements indicates that 16-18% of the free iso-amylamine has reacted (FIG. 1). In the presence of glycerol carbonate methacrylate, after 1 hour about 30% of the free iso-amylamine has reacted (FIG. 1). With glycerol carbonate, 37% of the iso-amylamine has reacted (FIG. 1). Based on heteronuclear $^1$H, $^{13}$C 2D NMR spectroscopy the corresponding formation of an urethane structure has been confirmed.

A larger amount of iso-amylamine has been reacted with compound of formula (I) and the reaction is faster compared to the reaction with cylocarbonate prior art. The compounds of formula (I) are more reactive with a primary amine than those known heretofor. As a consequence, the malodour generated by the amine compounds is more rapidly eliminated.

Example 2

NMR Monitoring of the Reaction of Compounds of Formula (I) or Prior Art Methycrylate Compounds with iso-amylamine in Solution Patent EP2542704A2 claims the efficacy of α,β unsaturated carbonyl moieties in counteracting thiol- and amine-based malodors in consumer, industrial and textile products. The reactivity of glycerol cyclocarbonate according to the invention was compared with one of the products disclosed in this prior art, the poly-(ethylene glycol) methylester methacrylate (Mw=300).

Figure 2:
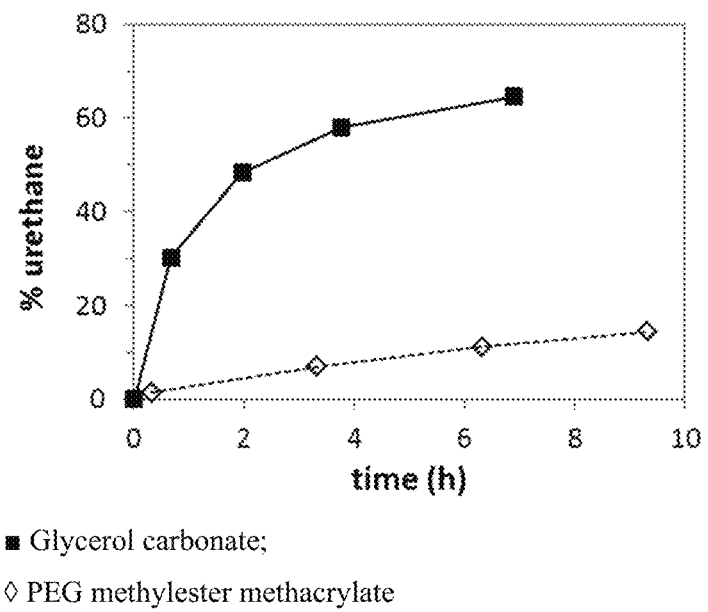
FIG. 2: Represents the conversion of iso-amylamine in presence of glycerol carbonate or PEG methylester methacrylate over time.

0.5 mol/l of iso-amylamine is dissolved in the NMR solvent methanol-d4. An equimolar amount of PEG methylester methacrylate is added, and the mixture is transferred to an NMR tube. A series of quantitative $^1$H-NMR spectra is carried out at 25° C. The trend of the measurements indicates that after 1 hour about 3% of the free iso-amylamine has reacted (FIG. 2).

It can be concluded from this experiment that the glycerol carbonate corresponding to a compound of formula (I) according to the present invention wherein R represents a hydrogen atom, is much more reactive with primary amines than a PEG methylester methacrylate reported as a compound to counteract amine-based malodors. Malodour has been neutralized more quickly and more malodour has been neutralized for an equivalent molar amount of active ingredient.

Example 3

Reaction Trough the Vapor Phase of bis((2-oxo-1,3-dioxolan-4-yl)methyl) Terephthalate with Iso-Amylamine In an hermetic 20 mL glass vial A, 0.02 g of iso-amylamine (malodour, liquid) were placed. A smaller, open glass vial B, was then placed into the bigger vial A. It contained 0.04 g of bis-carbonate terephtalate (compound of formula (I), fine powder). The vial A was sealed and left to equilibrate for 1 day. After 16 hrs at room temperature, an increased weight in the small vial B was measured corresponding to plus 94.2±1.6% of the weight of malodour initially present in vial A. IR analysis of the liquid present in the small vial B showed the apparition of a large peak around 3350 cm$^{-1}$, corresponding to the vibration of secondary amine bonds, and a strong peak around 1700 cm$^{-1}$, corresponding to the vibration of the C=O bond in urethane group. It was therefore concluded that:

Malodour has been transferred to the adsorbent (active ingredient) through the vapour phase.

Reaction has occurred at room temperature to form a hydroxyurethane.

Strong reduction of bad smell after 1 day in the presence of compound of formula (I) was also clearly olfactory measured in vial A, by panelists.

Example 4

Performance of Glycerol Carbonate (Compound of Formula (I)) Compared to Control Glycerol In two different 2 L glass jars, was placed a small glass cup containing 0.014 g of iso-amylamine (malodour, liquid). The jars were hermetically sealed and left to equilibrate overnight at room temperature. In the first jar, a solution ethanol/glycerol 50/50 wt. was sprayed 3 times (control). In the second jar, a solution ethanol/glycerol carbonate 50/50 wt. was sprayed. Jars were then sealed again and left for 2 h equilibration at room temperature before sensory evaluation.

12 panellists were asked to open and smell the two jars, and evaluate the malodour intensity on a 0 (no smell) to 10 (strong smell) scale.

Figure 3:
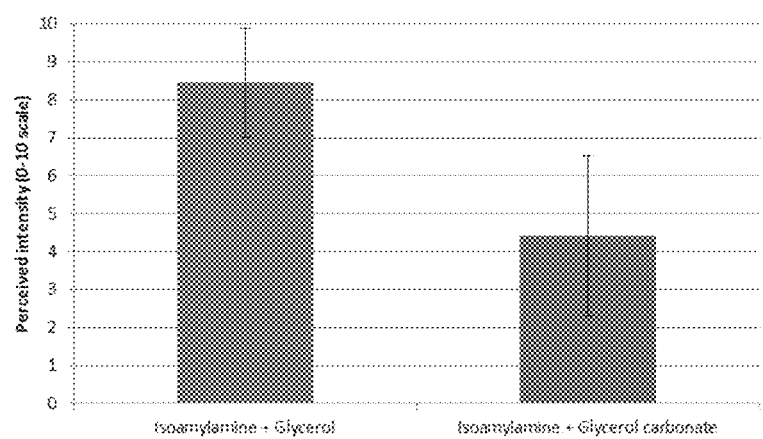
FIG. 3: Illustrates the perceived intensity of isoamylamine malodour in presence of glycerol or glycerol carbonate.

The results were that (FIG. 3):

The panelists identified the sample containing glycerol carbonate as less strong in intensity, less pungent "ammonia" smell.

A significant difference of about 4 units on the 0-10 scale was found on average.

Example 5

Kinetic of Reaction Between Glycerol Carbonate and Ammonia

In a 10 ml glass vial, 4 g of a 3% wt. ammonia solution was deposited. The pH was adjusted to 10.3. 1 g of glycerol carbonate was added and the sample was mixed manually. Aliquots of the solution were collected to measure IR spectrum of the solution over 48 hrs. A clear reduction of IR absorption band at around 1778 cm$^{-1}$ was measured. It is explained by the progressive disappearance of cyclo-carbonate functions. A peak shoulder at around 1696 cm$^{-1}$ is appearing and increases as a function of time. It is associated with the increasing amount of urethane functions in solution.

Figure 4:
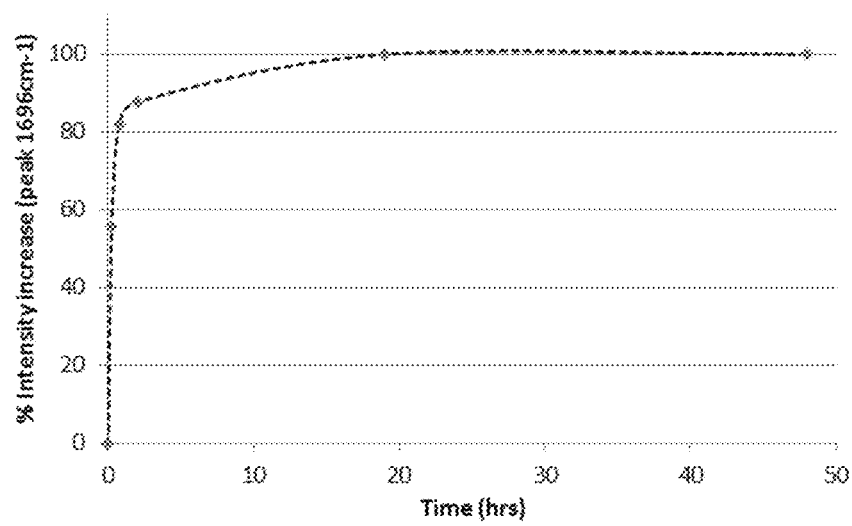
FIG. 4: Represents the intensity increase of IR absorption at 1696 $cm^{-1}$ over time

Referring to the peak intensities (IR absorption) over time and taking as reference point the IR absorption measured after 48 hrs (end of reaction), it is possible to plot the relative intensities compared to the reference point at a specific wavenumber (FIG. 4).

This intensity variation can be roughly associated to the kinetics of reaction of glycerol carbonate with ammonia in solution.

Since glycerol carbonate is here in molar excess compared to ammonia, the intensity increase of IR absorption at 1696 cm$^{-1}$, associated with urethane formation, should be in direct relation with the ammonia reduction in solution. It indicates that about 90% of the ammonia present in solution has reacted with glycerol carbonate after about 2 hrs.

A reference solution of glycerol carbonate in water at pH 10.3 was prepared likewise and IR absorption was followed over time. No difference in absorption pattern was measured after 48 hrs.

Example 6

Hair Coloring Preparation Comprising Invention's Compound

Glycerol carbonate (1 g) was added to an hair coloring formulation comprising ammonia (4 g, Table 1). The solution was mixed for 30 s using a spatula to obtain a homogeneous mixture. A reference mix was prepared in a separated vial by mixing glycerol (1 g) to the hair coloring formulation comprising ammonia (4 g, Table 1). The samples were hermetically closed and were let to equilibrate for 30 minuets. The malodor intensity was then evaluated on the opened samples by 3 panelists. The result showed a strong reduction of the pungent smell of ammonia for the sample comprising glycerol carbonate.

TABLE 1

Composition of the hair coloring formulation

| Ingredient | % wt. |
| --- | --- |
| Water deionized | 50.2 |
| Cetearyl alcohol | 8.00 |
| Lauric acid | 5.00 |
| Glycol distearate | 2.00 |
| Oleth-25 | 1.00 |
| Laureth-10 | 5.00 |
| Carbopol Ultrez 21 polymer 3% aqueous solution | 10.00 |
| Deceth-3 | 5.00 |
| Propylene glycol | 3.00 |
| Polyquaternium-22 | 0.5 |
| Pentasodium Pentetate | 0.3 |
| Ammonium hydroxide 30% aqueous solution | 10.00 |

Example 7

Malodor Reduction Efficacy Test of an Aerosol Air Freshener Comprising Glycerol Carbonate (Compound of Formula (I)) Versus a Control.

An aerosol air freshener comprising glycerol carbonate was prepared according to the formulation of table 2.

TABLE 2

Composition of the aerosol air freshener formulation

| Ingredient | Percent by Weight |
| --- | --- |
| Deionized Water | 73.96 |
| Sodium Borate | 0.37 |
| Sodium Molybdate | 0.08 |
| JEFFSOL ® GLYCERINE CARBONATE[1] (GC) | 0.50 |
| Emulsogen OG ™[2] | 0.50 |
| Propylene Glycol | 0.09 |
| Butane 46 | 24.50 |
| Total | 100.00 |

[1] 4-hydroxymethyl-1,3-dioxolan-2-one; origin: Huntsman
[2] oleic acid polyglycerine ester emulsifier; origin: Clariant A control formulation was prepared wherein the glycerol carbonate was replaced with deionized water.

The above components were filled into typical 3-piece tinplate aerosol cans with an optimized valve and actuator combination.

Both formulations produced a two-layered oil/water composition in the can. On agitation of the can a temporary mixture of the layers is achieved which will improve the spray performance of the aerosol.

The efficacy of the formulations at reducing the perception of fish malodor was assessed following the practices described in ASTM E 1593-06 "Method for Assessing the Efficacy of Air Care Products in Reducing Sensorly Perceived Indoor Air Malodor Intensity". Four 2000 $cm^3$ glass jars were used for the sensory evaluation of samples. Each glass jar contained a smaller 30 $cm^3$ wide-mouth glass jar containing 2 g of cod filet (that had been aged at ambient temperature for 24 hours). One jar was identified as a reference; the other three 'test' jars were labeled with randomly generated 3 digit codes.

One of the aerosols was sprayed for 1 second into one of the test jars. The other aerosol was sprayed into a second test jar for 1 second. Each of the four jars was then closed with aluminum foil.

The jars were allowed to equilibrate for 1 hour prior to assessment by a panel of 28 untrained but experienced assessors. By "untrained but experienced assessors" we mean individuals who have not received formal olfactive training but who are used to participating in fragrances assessments and have experience in rating the odor attributes. All assessors were first instructed to remove the foil and smell the odor in the reference jar, in order to familiarize themselves with the malodor. They were then instructed to remove the foil from the test sample jars and rate the intensity of the malodor using an un-labelled continuous 0-10 line scale, where 0 indicates no perceivable malodor and 10 indicates very strong malodor. Presentation of the test jars was blind, balanced, randomized, and sequential monadic.

Figure 5:
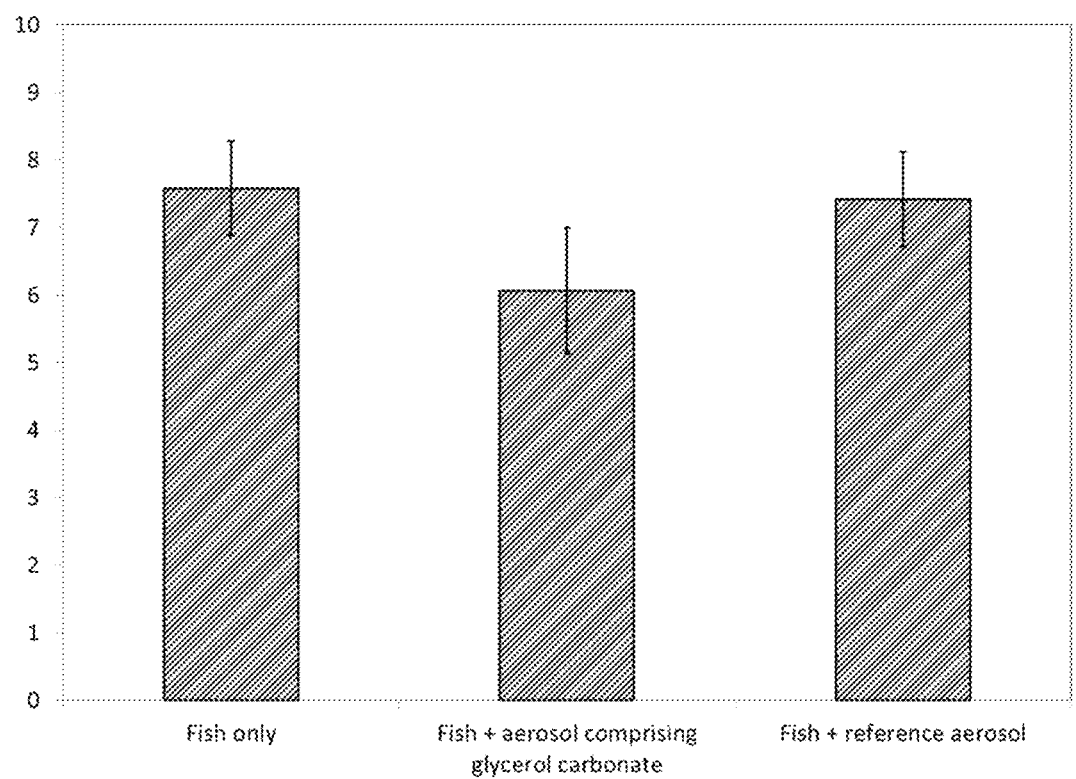
FIG. 5: Represent malodor intensity of the three test samples; i.e. sample 1 being fish, sample 2 being fish and aerosol air freshener comprising compound of formula (I) and sample 3 being fish and control aerosol air freshener (air freshener without compound of formula (I)).

Data was analyzed using Analysis of Variance (ANOVA) with Duncan's post-hoc analysis ($\alpha$=0.05). Mean malodor intensity of the three test samples is shown in FIG. 5.

The perceived malodor intensity of the jar treated with the reference aerosol was not significantly different (p>0.05) to the malodor only jar; thus, the aerosol formulation alone has no effect on the perceived malodor intensity.

The perceived malodor intensity of the jar treated with the aerosol comprising 0.5% by weight glycerol carbonate (compound of formula (I)) was significantly lower (p=0.0003) than the malodor only jar and the jar treated with the reference aerosol; thus, glycerol carbonate is useful in reducing the perception of fish malodor.

Example 8

Reduction of Ammonia Malodor Using Cat-Litter Comprising Glycerol Carbonate (Compound of Formula (I)).

A cat-litter composition comprising glycerol carbonate was prepared by admixing 5 g of glycerol carbonate with 95 g of virgin clay cat-litter.

20 g of the litter comprising glycerol carbonate was added to a 500 ml wide-mouth glass jar. A reference jar comprising 20 g of virgin clay cat litter was also prepared.

10 ml of a 0.5% by weight ammonium hydroxide solution was poured onto the litter in each of the jars. The jars were capped and allowed to equilibrate for 1 hour at ambient temperature.

The odor in the jars was assessed by a panel of 18 untrained but experienced assessors. By "untrained but experienced assessors" we mean individuals who have not received formal olfactive training but who are used to participating in fragrances assessments and have experience in rating the odor attributes.

The assessors were instructed to assess the jars in a random order and indicate which of the jars had the lowest ammonia odor perception. All 18 assessors selected the jar containing the cat-litter comprising 5% by weight glycerol carbonate as having the least ammonia odor. Glycerol carbonate is effective at reducing the perception of ammonia in cat-litter application.

The invention claimed is:

1. A method to reduce or reduce malodour from ammonia, primary amines, or secondary amines, comprising: dispensing in a closed space or applying to a surface an effective amount of at least one compound of formula

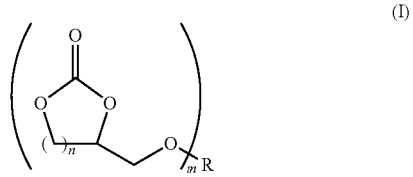

(I)

wherein m is an integer from 1 to 4; n is 1 or 2; and R represents a hydrogen atom or a $C_{1-10}$ hydrocarbon group, the hydrocarbon group optionally comprising one or two oxygen or nitrogen atoms.

2. The method according to claim 1, wherein m is 1 or 2.

3. The method according to claim 1, wherein n is 1.

4. The method according to claim 1, wherein R represents a hydrogen atom or a $C_{3-8}$ hydrocarbon group, optionally comprising one or two oxygens.

5. The method according to claim 1, wherein the compound of formula (I) is selected from the group consisting of 4-(hydroxymethyl)-1,3-dioxolan-2-one, (2-oxo-1,3-dioxolan-4-yl)methyl methacrylate, 4,4'-((1,3-phenylenebis(oxy))bis(methylene))bis(1,3-dioxolan-2-one) and bis((2-oxo-1,3-dioxolan-4-yl)methyl) terephthalate.

6. The method according to claim 1, wherein the compound of formula (I) is used in combination with a malodor counteracting composition comprising at least one ingredient selected from Group (I), at least one ingredient selected from Group (II), and at least one ingredient selected from Group (III), wherein Groups (I) to (III) are defined as follows:

a) Group (I): aldehydes of formula $R^1CHO$, wherein $R^1$ is an aliphatic linear or branched, saturated or unsaturated carbon chain containing from 1 to 12 carbon atoms;
b) Group (II): ketones of formula $R^2COR^3$, wherein $R^2$ is an ethyl or methyl group and $R^3$ is an aliphatic linear or branched, saturated or unsaturated carbon chain containing from 1 to 12 carbon atoms;
c) Group (III): primary alcohols of formula $R^4CH_2OH$, wherein $R^4$ is an aliphatic linear or branched, saturated or unsaturated carbon chain containing 1 to 12 carbon atoms, optionally substituted with an aromatic moiety.

7. The method according to claim 1, wherein the effective amount of at least one compound of formula (I) is dispensed in a closed space by a spraying device.

8. A malodor neutralizing composition comprising:
a) at least one compound of formula (I);
b) at least one ingredient selected from the group consisting of a carrier, a perfumery ingredient, a perfumery adjuvant, and a mixture thereof; and
c) optionally at least one additional malodour counteractant composition.

9. The malodor neutralizing composition according to claim 8, wherein the composition comprises at least one compound of formula (I) in an amount between 0.1% and 50% by weight, relative to the total weight of the composition, and at least one solid carrier.

10. The malodor neutralizing composition according to claim 8, wherein the solid carrier is an absorbent material obtained from processed corncob.

11. A malodor neutralizing consumer product comprising at least one compound of formula (I) according to claim 1.

12. The malodor neutralizing consumer product according to claim 11, wherein the consumer product is a fabric care product, a body-care product, a skin-care product, an air care product, a pet care product or a home care product.

13. The malodor neutralizing consumer product according to claim 11, wherein the consumer product is a fabric softener, a fabric refresher, an ironing water, an air freshener, a "ready to use" powdered air freshener, a shampoo, a coloring preparation, a hair spray, or a cat litter.

* * * * *